(12) United States Patent
Nantermet et al.

(10) Patent No.: US 6,403,612 B2
(45) Date of Patent: Jun. 11, 2002

(54) THROMBIN RECEPTOR ANTAGONISTS

(75) Inventors: Philippe G. Nantermet, Lansdale; James C. Barrow, Harleysville; Harold G. Selnick, Ambler, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/772,352

(22) Filed: Jan. 30, 2001

Related U.S. Application Data
(60) Provisional application No. 60/179,342, filed on Jan. 31, 2000.

(51) Int. Cl.⁷ ................ A61K 31/54; A61K 31/445; C07D 211/06; C07D 263/02; C07D 207/00

(52) U.S. Cl. ................ 514/317; 514/327; 514/330; 514/369; 514/375; 514/376; 514/422; 546/192; 546/226; 548/188; 548/200; 548/215; 548/230; 548/517; 548/538

(58) Field of Search .................. 548/517, 538, 548/188, 200, 215, 230; 546/192, 226; 514/317, 327, 330, 369, 375, 376, 422

(56) References Cited

U.S. PATENT DOCUMENTS

| | | | | |
|---|---|---|---|---|
| 4,910,190 A | * | 3/1990 | Bergeson et al. | 548/538 |
| 5,340,801 A | * | 8/1994 | Ewing et al. | 548/538 |
| 5,446,131 A | | 8/1995 | Maraganore | |
| 5,457,177 A | | 10/1995 | Veber et al. | |
| 5,516,889 A | | 5/1996 | Hollenberg et al. | |
| 5,866,681 A | | 2/1999 | Scarborough | |
| 6,017,890 A | | 1/2000 | Hoekstra et al. | |
| 6,063,847 A | | 5/2000 | Chackalamannil et al. | |
| 6,156,732 A | | 12/2000 | Hoekstra et al. | |

FOREIGN PATENT DOCUMENTS

WO    WO 94/03479    2/1994

OTHER PUBLICATIONS

Bernatowicz, Michael, S. et al., "Development of Potent Thrombin Receptor Antagonict Peptides", *J. Med. Chem.*, pp. 4879–4887; 39: 1996.

Alexopoulos, K. et al., "A comparative SAR study of thrombin receptor derived non peptide mimetics: Importance of phenyl/guanidino proximity for activity", *Amino Acids*, pp. 211–220; 15: 1998.

* cited by examiner

*Primary Examiner*—Alan L. Rotman
*Assistant Examiner*—Raymond Covington
(74) *Attorney, Agent, or Firm*—Richard S. Parr; Valerie J. Camara

(57) ABSTRACT

A thrombin receptor antagonist having the formula

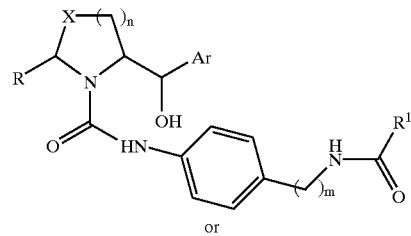

or

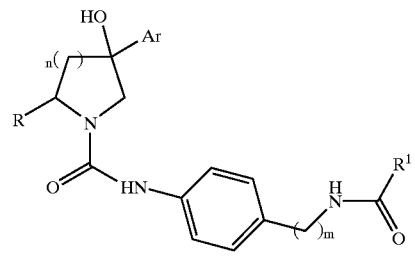

or a pharmaceutically acceptable salt thereof, useful for inhibiting the aggregation of blood platelets. The compounds can be used in a method of acting upon a thrombin receptor which comprises administering a therapeutically effective but non-toxic amount of such compound to a mammal, preferably a human.

5 Claims, No Drawings

THROMBIN RECEPTOR ANTAGONISTS

This application claims priority from Provisional application Ser. No. 60/179,342, filed Jan. 31, 2000.

SUMMARY OF THE INVENTION

Compounds of the invention are useful for inhibiting the aggregation of blood platelets. The above-mentioned compounds, which are thrombin receptor antagonists, can be used in a method of acting upon a thrombin receptor which comprises administering a therapeutically effective but non-toxic amount of such compound to a mammal, preferably a human. A pharmaceutical composition comprising a pharmaceutically acceptable carrier and, dispersed therein, an effective but non-toxic amount of active drug is another feature of this invention.

DETAILED DESCRIPTION OF THE INVENTION

The invention includes compounds having the formula

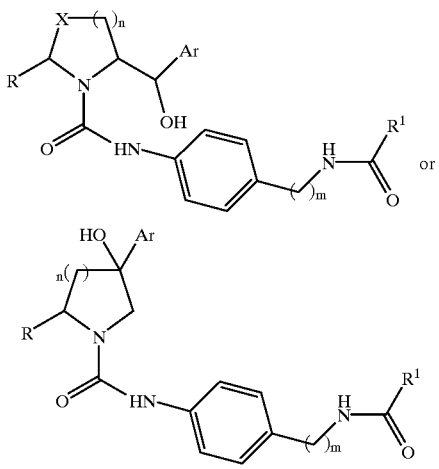

or a pharmaceutically acceptable salt thereof, wherein
m is 0, 1 or 2;
n is 1, 2 or 3;
R and $R^1$ are independently selected from the group consisting of
  hydrogen,
  $C_{1-10}$ alkyl,
  $C_{1-10}$ alkoxy,
  aryl, unsubstituted, monosubstituted, independently disubstituted or independently trisubstituted with
    $C_{1-10}$ alkyl,
    halogen,
    CN,
    $NO_2$,
    amino $C_{1-10}$ alkyl,
    $CF_3$,
    $COOR^3$, wherein $R^3$ is hydrogen or $C_{1-10}$ alkyl, or
    $C(O)R^3R^4$, wherein $R^3$ and $R^4$ are independently hydrogen or $C_{1-10}$ alkyl, or
    $S(O)_pR^3$, wherein $R^3$ is hydrogen or $C_{1-10}$ alkyl, and wherein p is 0, 1, or 2;
  halogen,
  $CF_3$,
  —$OCH_3$,
  —$SCH_3$,
  $SOCH_3$,
  $SO_2CH_3$, or
  CN;
X is
  $CH_2$,
  S,
  SO,
  $SO_2$,
  $CHOR^2$, wherein $R^2$ is hydrogen or $C_{1-10}$ alkyl; and
Ar is
  aryl, unsubstituted, monosubstituted, independently disubstituted or independently trisubstituted with
    $C_{1-10}$ alkyl,
    halogen,
    CN,
    $NO_2$,
    amino $C_{1-10}$ alkyl,
    $CF_3$,
    $COOR^5$, wherein $R^5$ is hydrogen or $C_{1-10}$ alkyl,
    $C(O)R^5R^6$, wherein $R^5$ and $R^6$ are independently hydrogen or $C_{1-10}$ alkyl, or
    $S(O)_pR^5$, wherein $R^5$ is hydrogen or $C_{1-10}$ alkyl, and wherein p is 0, 1, or 2, or
  heteroaryl, unsubstituted, monosubstituted, independently disubstituted or independently trisubstituted with
    $C_{1-10}$ alkyl,
    halogen,
    CN,
    $NO_2$,
    amino $C_{1-10}$ alkyl,
    $CF_3$,
    $COOR^7$, wherein $R^7$ is hydrogen or $C_{1-10}$ alkyl,
    $C(O)R^7R^8$, wherein $R^7$ and R4 are independently hydrogen or $C_{1-10}$ alkyl, or
    $S(O)_pR^7$, wherein $R^7$ is hydrogen or $C_{1-10}$ alkyl, and wherein p is 0, 1,or2.

In a class of compounds of the invention and pharmaceutically acceptable salts thereof,
  m is 1;
  n is 1 or 2;
  R is
    hydrogen, or
    $C_{1-10}$ alkyl;
  $R^1$ is $C(CH_3)_3$;
  X is
    $CH_2$,
    S,
    SO,
    CHOH,
    $CHOCH_3$; and
  Ar is
    aryl, unsubstituted, monosubstituted with halogen, or disubstituted same or different, with halogen.

In a group of this class of compounds and pharmaceutically acceptable salts thereof,
  R is
    hydrogen,
    $CH_3$, or
    $CH_2CH_3$; and Ar is
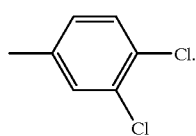
Specific embodiments of this group of compounds and pharmaceutically acceptable salts thereof include
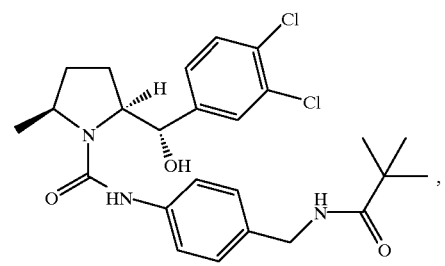
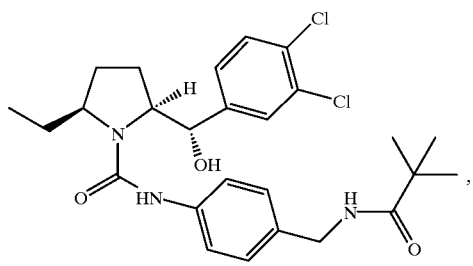
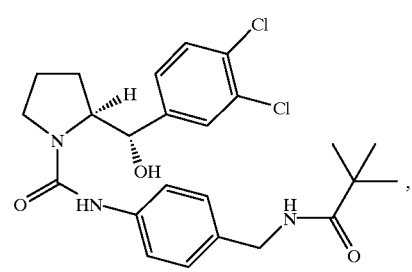
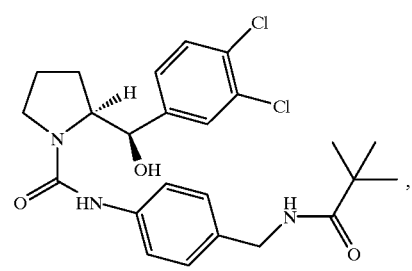
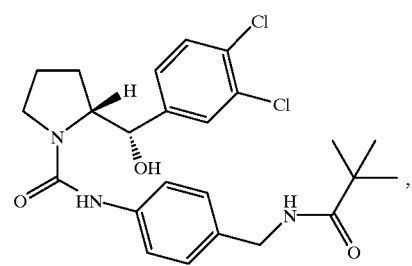
-continued
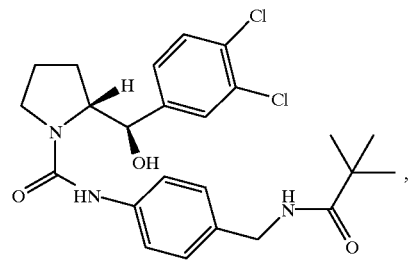
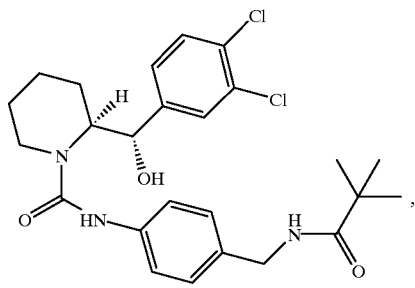
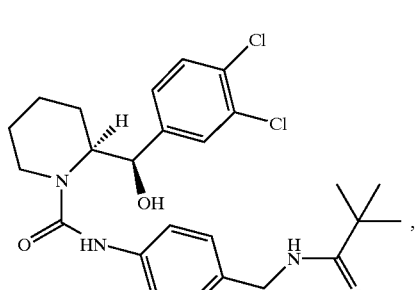
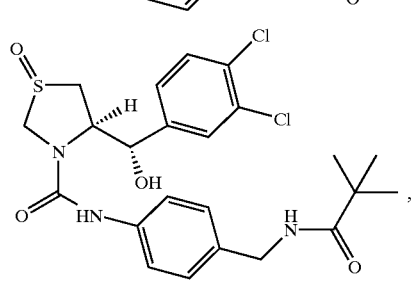
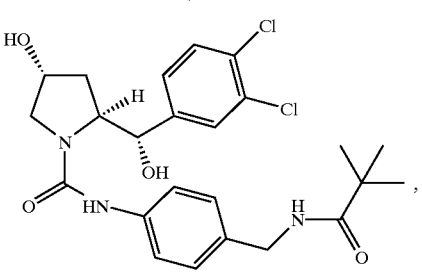

-continued

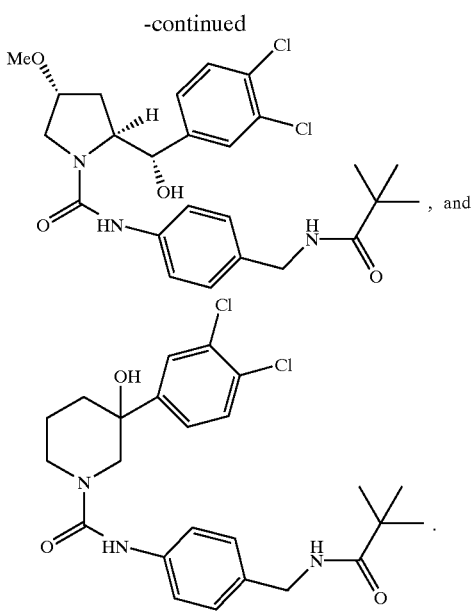
, and

The term "alkyl" means branched or straight-chain saturated aliphatic hydrocarbon groups having the specified number of carbon atoms (for example, "$C_{1-10}$" denotes alkyl having 1 to 10 carbon atoms, e.g., methyl, ethyl, n-propyl, isopropyl, n-butyl, isobutyl, sec-butyl, tert-butyl, pentyl, iso-amyl, hexy, octyl radicals and the like.

The term "alkenyl" means hydrocarbon chains of either a straight of branched configuration and one or more unsaturated carbon-carbon bonds which may occur at an stable point along the chain, e.g., propylenyl, buten-1-yl, isobutenyl, pentenylen-1-yl, 2,2-methylbuten-1-yl, 3-methylbuten-1-yl, hexen-1-yl, hepten-1-yl, and octen-1-yl radicals and the like.

The term, "alkynyl" means hydrocarbon chains of either a straight or branched configuration and one or more triple carbon-carbon bonds which may occur in any stable point along the chain, e.g., ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "alkoxy" means an alkyl group of indicated number of carbon atoms attached through an oxygen bridge, e.g., methoxy, ethoxy, n-propoxy, isopropoxy, n-butoxy, isobutoxy, sec-butoxy, tert-butoxy, pentyloxy, radicals and the like.

The terms "alkylene", "alkenylene", "phenylene", and the like, refer to alkyl, alkenyl, and phenyl groups, respectively, which are connected by two bonds to the rest of the structure. Such "alkylene", "alkenylene", "phenylene", and the like, may alternatively and equivalently be denoted herein as "—(alkyl)—", "—(alkenyl)—" and "—(phenyl)—", and the like.

The term "halogen" includes fluorine, chlorine, iodine and bromine.

The term "oxy" means an oxygen (O) atom.

The term "thio" means a sulfur (S) atom.

The term "aryl" means a partially saturated or fully saturated 6–14 membered ring system such as for example, phenyl, naphthyl or anthracyl. The term "Ph", which appears in certain chemical formulas in the specification and claims, represents phenyl.

The term "cycloalkyl" means saturated ring groups, including mono-, bi-, or poly-cyclic ring systems such as cyclopropyl, cyclobutyl, cyclopentyl, cyclohexy, cycloheptyl, cyclooctyl, adamantyl, and the like.

The term "heterocyclic" or "heterocycle" means a stable 5- to 7-membered monocyclic or bicyclic or 7- to 10-membered bicyclic heterocyclic ring which may be saturated, partially unsaturated, or aromatic, which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of heterocyclic rings include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, indolenyl, isoxazolinyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxanthiinyl, 2H-pyrrolyl, pyrrolyl, imidazolyl, pyrazolyl, isothiazolyl, isoxazolyl, oxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazole, carbazole, β-carbolinyl, phenanthridinyl, .acridinyl, perimidinyl, phenanthrolinyl, phenazinyl, phenarsazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl or oxazolidinyl. Also included are fused ring and spiro compounds containing, for example, the above heterocycles.

The term "heteroaryl" means an aromtaic heterocyclic group, preferably 5 or 6-membered monocyclic ring systems or 8–10 membered fused bicyclic groups, having heteroatoms selected from the group consisting of N, O, and S, for example, pyridyl (pyridinyl), pyrimidinyl, furanyl (furyl), thiazolyl, thienyl, pyrrolyl, pyrazolyl, imidazolyl, indolyl, isoxazolyl, oxazolyl, pyrazinyl, pyridazinyl, benzofuranyl, benzothienyl, benzimidazolyl, quinolinyl, or isoquinolinyl.

Under standard nonmenclature used throughout this disclosure, the terminal portion of the designated side chain is described first followed by the adjacent functionality toward the point of attachment. For example, a methylene substituted with ethylcarbonylamino is equivalent to

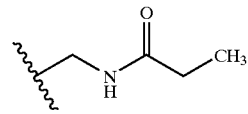

Compounds of the present invention may be chiral; included within the scope of the present invention are racemic mixtures and separated enantiomers of the general formula. Furthermore, all diastereomers, including E, Z isomers, of the general formula are included in the present scope. Furthermore, hydrates as well as anhydrous compositions and polymorphs of the general formula are within the present invention. Thus, the term "active drug" includes a compound of the invention and its salts, racemic mixtures or separated enantiomers, hydrates or anhydrous forms, polymorphs, and pharmaceutically acceptable salts.

The term "pharmaceutically acceptable salts" shall mean non-toxic salts of the compounds of this invention which are generally prepared by reacting the free base with a suitable organic or inorganic acid. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

Prodrugs, such as ester derivatives of active drug are compound derivatives which, when absorbed into the bloodstream of a warm-blooded animal, cleave in such a manner as to release the drug form and permit the drug to afford improved therapeutic efficacy.

The term "pharmaceutically effective amount" shall mean that amount of a drug or pharmaceutical agent that will elicit the biological or medical response of a tissue, system or animal that is being sought by a researcher or clinician. The term "anti-coagulant" shall include heparin, and warfarin. The term "thrombolytic agent" shall include agents such as streptokinase and tissue plasminogen activator. The term "platelet anti-aggregation agent" shall include agents such as aspirin and dipyridamole.

In the schemes and examples below, various reagent symbols have the following meanings:
BOC
(or Boc): t-butyloxycarbonyl
Pd-C: Palladium on activated carbon catalyst
DMF: Dimethylformamide
DMSO: Dimethylsulfoxide
CBZ: Carbobenzyloxy
$CH_2Cl_2$: Methylene chloride
$CHCl_3$: chloroform
EtOH: ethanol
MeOH: methanol
EtOAc: ethyl acetate
HOAc: acetic acid
BOP: Benzotriazol-1-yloxytris(dimethylamino) phosphonium, hexafluorophosphate
EDC: 1-(3-Dimethylaminopropyl)-3-ethylcarbodiimide hydrochloride
Oxone: potassium peroxymonosulfate
LDA: Lithium diisopropylamide Active drug can be administered in such oral forms as tablets, capsules (each of which includes sustained release or timed release formulations), pills, powders, granules, elixirs, tinctures, suspensions, syrups, and emulsions. Likewise, it may be administered in intravenous (bolus or infusion), intraperitoneal, subcutaneous, or intramusculsar form, all using forms well known to those of ordinary skill in the pharmaceutical arts. An effective but non-toxic amount of active drug can be employed as an anti-aggregation agent.

Active drug may be administered to patients where prevention of thrombosis by inhibiting thrombin activation of the thrombin receptor is desired. It is useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Active drug may be administered to these surgical patients to prevent the formation of thrombi and thromboemboli.

Other applications of active drug include prevention of platelet thrombosis, thromboembolism and reocclusion during and after thrombolytic therapy and prevention of platelet thrombosis, thromboembolism and reocclusion after angioplasty or coronary artery bypass procedures. It may also be used to prevent myocardial infarction.

The dosage regimen utilizing active drug is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of active drug when used for the indicated effects, will range between about 0.005 mg per kg of body weight per day (mg/kg/day) to about 50 mg/kg/day and preferably 0.005–20 mg/kg/day and most preferably 0.005–10 mg/kg/day. For example, a typical 90 kg patient would receive oral dosages ranging between about 0.45 mg/day and about 4.5 g/day, most preferably between about 1.0 mg/day and 1.0 g/day. Suitable pharmaceutical oral compositions such as tablets or capsules may contain 1–500 mg, for example, 1 mg, 10 mg, 100 mg, 200 mg and 500 mg. Intravenously, the most preferred doses will range from about 0.5 to about 5 mg/kg/minute during a constant rate infusion. Active drug may be administered in one or divided doses of two, three, or four times daily. Furthermore, active drug can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather that intermittent throughout the dosage regime.

In the methods of the present invention, the active drug can form the active ingredient, and is typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distinegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The active drug can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Active drug may also be delivered by the use of monoclonal antibodies as individual carriers to which the compound molecules are coupled. Active drug may also be coupled with soluble polymers as targetable drug carriers. Such polymers can include polyvinyl-pyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates and cross linked or amphipathic block copolymers of hydrogels.

Active drug can also be co-administered with the usual doses of suitable anticoagulation agents, such as heparin or warfarin (typically given in tablet doses between 1 and 20 mg daily during administration of the active drug), or thrombolytic agents such as tissue plasminogen activator (typically given in i.v. doses of between 20 and 150 mg over two hour period prior to or during administration of the active drug), to achieve beneficial effects in the treatment of various vascular pathologies. Such co-administration also includes administration if the active drug with doses of anticoagulant agents or thrombolytic agents less than the usual doses of those agents.

Compounds of the invention were prepared according to the following general schemes, including the specific procedures described in the following examples. Those skilled in the art will readily understand that known variations of the conditions and processes of the following preparative procedures can be used to prepare these compound. All temperatures are degrees Celsius unless otherwise noted.

The proposed ureas of type 5 can be prepared according to the following general scheme 1. Cyclic amino acids of type 1 are converted to the corresponding Weinreb amides of type 2, after N-Boc protection. Lithium halogen exchange on an aryl halide followed by addition to the previous Weireb amide, reduction of the resulting ketone with NaBH$_4$, and Boc removal with HCl (g) leads to aminoalcohol derivative of type 3. Coupling with isocyanate 4 provides ureas of type 5. Alternatively, 3 can be converted to the cyclic oxazolidinone 6 thus allowing stereochemical assignments using 1H NMR NOE and 2D techniques. Isocyanate 4 is easily prepared from any aniline using phosgene as shown below.

General Scheme 1

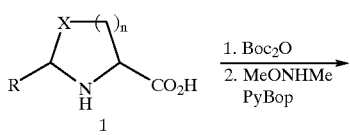

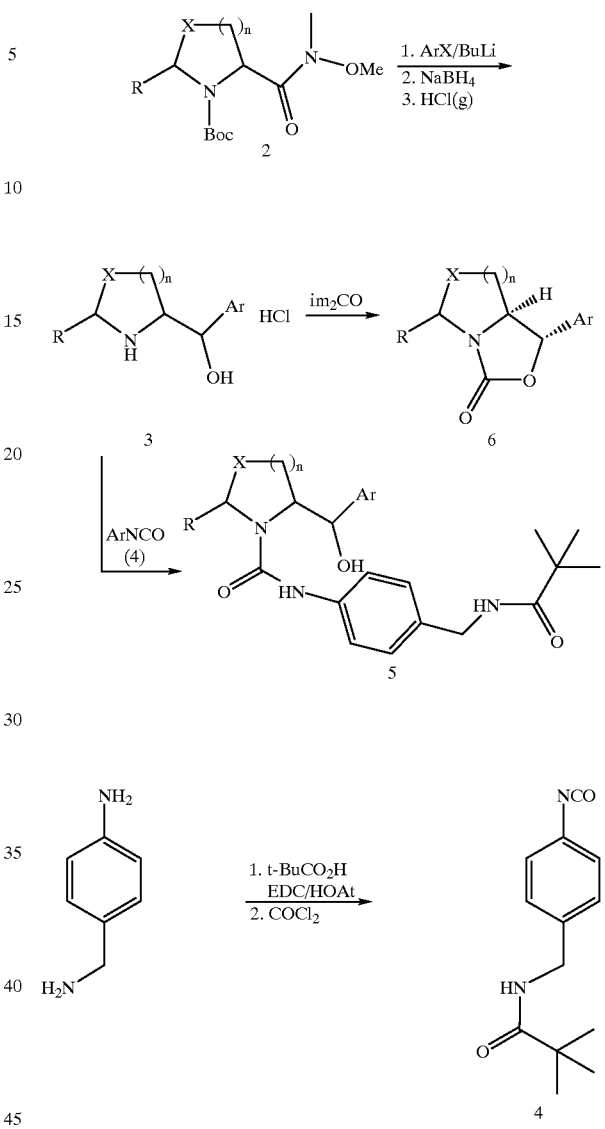

The proposed ureas of type 9 can be prepared according to the following general scheme 2. Amino alcohols derivatives of type 7 are oxidized to the corresponding ketones of type 8 after Boc protection. Lithium halogen exchange on an aryl halide followed by addition to the previous ketone provides the corresponding benzyl alcohols which can be coupled to isocyanates of type 4 after Boc removal to give ureas of type 9, as shown below.

General Scheme 2

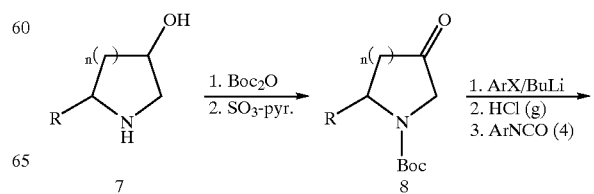

-continued

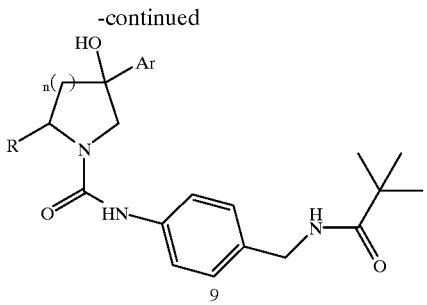

9

EXAMPLE 1a

2(S)-[(3,4-dichlorophenyl)-(S)hydroxymethyl]-5(S)-methyl-pyrrolydine-1-carboxylic acid {4-[(2,2-dimethyl-propionylamino)-methyl]-phenyl}-amide

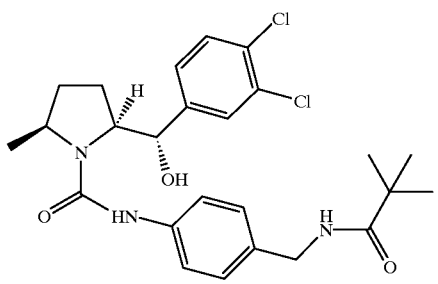

N-methoxylcabonyl-5(RS)-methyl-pyrrolydine-2(S)-carboxylic acid methyl ester is prepared as a diastereomeric mixture at C-5, according to the procedure of Y. Kikugawa et al (*Tetrahedron Lett.* 1997, 38, 6677–6680)

A suspension of N-methoxylcarbonyl-5(RS)-methyl-pyrrolydine-2(S)-carboxylic acid methyl ester (3 g, 14.9 mmol) in 6 N HCl (100 ml) is refluxed for 18 hrs. The reaction mixture is concentrated in vacuo and flushed/concentrated with dioxane 3 times to give 5(RS)-methyl-pyrrolydine-2(S)-carboxylic acid hydrochloride (2 g) which is used as is in the next step To a suspension of 5(RS)-methyl-pyrrolydine-2(S)-carboxylic acid hydrochloride (2 g, 12 mmol) in dioxane (38 ml) and water (24 ml) is added 5 N NaOH (3 ml, 15 mmol) and dit-butyl carbonate (2.8 g, 13 mmol) and the reaction mixture is stirred at 25° C. for 30 min. 5 N NaOH (1.5 ml, 7.5 mmol) is added and the reaction mixture is stirred at 25° C. for 18 hrs. The reaction mixture is concentrated in vacuo to remove dioxane, further diluted with water and extracted with pentane. The aqueous layer is acidified with 10% citric acid and extracted 3 times with ethyl acetate. The combined organic layer is washed with brine, dried over sodium sulfate and concentrated in vacuo to give N-t-butoxycarbonyl-5(RS)-methyl-pyrrolydine-2(S)-carboxylic acid (1.3 g) which is used as is in the next step.

To a solution of N-t-butoxycarbonyl-5(RS)-methyl-pyrrolydine-2(S)-carboxylic acid (1.3 g, 5.7 mmol) in methylene chloride (40 ml) is added diisopropyl ethylamine (3 ml, 17.1 mmol), PyBrOP (2.8 g, 6 mmol) and O,N-dimethylhydroxylamine hydrochloride (0.72 g, 7.4 mmol) and the reaction mixture is stirred at 25° C. for 18 hrs. The reaction mixture is concentrated in vacuo, diluted with ethyl acetate, washed with 1 N HCl, with aqueous sodium bicarbonate, water and brine, dried over sodium sulfate and concentrated in vacuo. The crude product is purified by flash chromatography (silica gel, 25% to 30% ethyl acetate in hexane) to give N-t-butoxycarbonyl-5(RS)-methyl-pyrrolydine-2(S)-carboxylic acid methoxy-methyl-amide (950 mg).

$^1$H NMR (CDCl$_3$, 300 MHz) ca. 1:1 mixture of rotomers: □4.80–4.65 (m, 0.5 H); 4.65–4.55 (m, 0.5 H); 4.25–3.85 (m, 1 H); 3.80 (s, 0.75 H); 3.78 (s, 0.75 H); 3.72 (s, 1.5 H); 3.22 (s, 1.5 H); 3.18 (s, 1.5 H); 2.30–1.80 (m, 3 H); 1.80–1.60 (m, 1 H); 1.45 (s, 4.5 H); 1.40 (s, 4.5 H); 1.35–1.30 (m, 1.5 H); 1.20 (d, 0.75 H); 1.16 (d, 0.75 H).

To a solution of 3,5-dichloro iodobenzene (4.8 g, 17.5 mmol) in diethyl ether (38 ml) cooled to −78° C. is added n-BuLi (7 ml of a 2.5 M solution in hexane, 17.5 mmol). The reaction mixture is stirred at −78° C. for 10 min and allowed to warm to 0° C. A portion of the previous solution (11 ml) is added to a solution of N-t-butoxycarbonyl-5(RS)-methyl-pyrrolydine-2(S)-carboxylic acid methoxy-methyl-amide (950 mg, 3.5 mmol) in diethyl ether (38 ml) cooled to 0° C. and the resulting reaction mixture is stirred at 0° C. for 45 min. The reaction mixture is quenched with water, extracted with ethyl acetate and the organic layer is extracted, washed with brine, dried over sodium sulfate and concentrated in vacuo. The crude product is purified by flash chromatography (silica gel, 2% ethyl acetate in hexane) to give N-t-butoxycarbonyl-2(S)-[(3,4-dichlorophenyl)-carbonyl]-5(S)-methyl-pyrrolydine (198 mg, lower Rf) and N-t-butoxycarbonyl-2(S)-[(3,4-dichlorophenyl)-carbonyl]-5(R)-methyl-pyrrolydine (98 mg, upper Rf).

5(S) isomer: $^1$H NMR (CDCl$_3$, 300 MHz) ca. 1:1 mixture of rotomers: δ8.05 (b d, 1 H); 7.85–7.75 (m, 1 H); 7.60–7.50 (m, 1 H); 5.25 (t, 0.5 H); 5.15 (t, 0.5 H); 4.15–4.05 (m, 0.5 H); 4.05–3.95 (m, 0.5 H); 2.30–2.20 (m, 1 H); 2.20–2.00 (m, 1 H); 2.00–1.80 (m, 1 H); 1.75–1.60 (m, 1 H); 1.45 (s, 4.5 H); 1.37 (d, 1.5 H); 1.33 (d, 1.5 H); 1.25 (s, 4;.5 H).

To a solution of N-t-butoxycarbonyl-2(S)-[(3,4-dichlorophenyl)-carbonyl]-5(S)-methyl-pyrrolydine (190 mg, 0.53 mmol) in methanol (10 ml) is added sodium borohydride (24 mg, 0.64 mmol) and the reaction mixture is stirred at 25° C. for 1 hr. Some more sodium borohydride is added and the reaction mixture is stirred at 25° C. for 30 min. After quenching with acetone, the reaction mixture is concentrated in vacuo. The residue is taken in ethyl, washed with aqueous sodium bicarbonate, water and brine, dried over sodium sulfate and concentrated in vacuo to give N-t-butoxycarbonyl-2(S)-[(3,4-dichlorophenyl)-(S) hydroxymethyl]-5(S)-methyl-pyrrolydine (200 mg) containing ca. 10% of the corresponding (R)hydroxymethyl isomer. $^1$H NMR (CDCl$_3$, 400 MHz): δ7.50 (d, 1 H); 7.40 (d, 1 H); 7.20 (dd, 1 H); 6.25 (b s, 1 H); 4.45 (d, 1 H); 4.00–3.90 (m, 2 H); 2.00–1.80 (m, 1 H); 1.60–1.40 (m, 3 H); 1.50 (s, 9 H); 1.20 (d, 3 H).

Through a solution of N-t-butoxycarbonyl-2(S)-[(3,4-dichlorophenyl)-(S)hydroxymethyl]-5(S)-methyl-pyrrolydine (200 mg, 0.56 mmol) in methylene chloride (15 ml) cooled to 0° C. is bubbled HCl (g) for 5 min. The reaction mixture is stirred at 25° C. for 1.5 hr and the process is repeated. After 30 min stirring at 25° C., the reaction mixture is concentrated in vacuo and flushed with methylene chloride/concentrated 3 times to provide 2(S)-[(3,4-dichlorophenyl)-(S)hydroxymethyl]-5(S)-methyl-pyrrolydine hydrochloride which is used as is in the next reaction.

To a solution of 2(S)-[(3,4-dichlorophenyl)-(S) hydroxymethyl]-5(S)-methyl-pyrrolydine hydrochloride (78 mg, 0.26 mmol) in methylene chloride (18 ml) is added triethyl amine (54 ul, 0.39 mmol) and N-(4-isocyanato-benzyl)-2,2-dimethyl-propionamide (2.6 ml, 0.1M in methylene chloride, 0.26 mmol). The reaction mixture is stirred at 25° C. for 30 min and concentrated in vacuo. The crude product is purified by flash chromatography (silica gel, 2% to 3% isopropanol in chloroform) to give 2(S)-[(3,4-dichlorophenyl)-(S)hydroxymethyl]-5(S)-methyl-pyrrolydine-1-carboxylic acid {4-[(2,2-dimethyl-propionylamino)-methyl]-phenyl}-amide (57 mg) as a white solid.

MS (FAB): M+1 492.2 for $C_{25}H_{31}Cl_2N_3O_3$

N-(4-isocyanato-benzyl)-2,2-dimethyl-propionamide is prepared as follows:

To a solution of trimethyl acetic acid (9.98 g, 97.7 mmol) in methylene chloride (200 ml) cooled to 0° C. is added 4-aminobenzyl amine (11.1 ml, 97.7 mmol), triethyl amine (34.1 ml, 244 mmol), HOAt (13.3 g, 97.7 mmol), and EDC (18.73 g, 97.7 mmol). The reaction mixture is allowed to slowly warm to 25° C. and stirred at this temperature for 18 hrs. The reaction mixture is diluted with water and the organic layer is extracted, washed with aqueous sodium bicarbonate and brine, dried over magnesium sulfate and concentrated in vacuo. The crude product is purified by flash chromatography (silica gel, 40% to 65% ethyl acetate in hexane) to give N-(4-amino-benzyl)-2,2-dimethyl-propionamide (16.8 g), as a pale yellow solid.

$^1$H NMR (CDCl$_3$, 300 MHz): δ7.15 (d, 2 H); 6.65 (d, 2 H); 5.75 (b s, 1 H); 4.30 (d, 2 H); 3.65 (b s, 2 H); 1.20 (s, 9 H).

To a solution of phosgene (24.1 ml of a 1.93 M solution in toluene, 46.5 mmol) in methylene chloride (50 ml) cooled to 0° C. is added dropwise a solution of N-(4-amino-benzyl)-2,2-dimethyl-propionamide (8 g, 38.8 mmol) and triethyl amine (13.5 ml, 97 mmol) in methylene chloride (80 ml). The reaction mixture is allowed to slowly warm to 25° C. and stirred at this temperature for 18 hrs. The reaction mixture is filtered on dry cellite, under an argon atmosphere and the filtrate is concentrated in vacuo. The residue is dissolved in methylene chloride (380 ml) to provide a 0.1 M solution of N-(4-isocyanato-benzyl)-2,2-dimethyl-propionamide in methylene chloride which is used as is.

To a solution of 2(S)-[(3,4-dichlorophenyl)-(S) hydroxymethyl]-5(S)-methyl-pyrrolydine hydrochloride (79 mg, 0.27 mmol) in methylene chloride (5 ml)) is added triethyl amine (44 ul, 0.32 mmol) and carbonyl diimidazole (110 mg, 0.68 mmol). The reaction mixture is stirred at 25° C. for 18 hrs, concentrated in vacuo and the residue product is purified by flash chromatography (silica gel, 30% ethyl acetate in hexane) to give 1(S)-(3,4-dichloro-phenyl)-5(S)-methyl-tetrahydro-pyrrolo[1,2(S)-c]oxazol-3-one.

$^1$H NMR (CDCl$_3$, 500 MHz): δ7.48 (d, 1 H); 7.47 (d, 1 H); 7.21 (dd, 1 H); 5.13 (d, 1 H); 4.00–3.92 (m, 1H); 3.87–3.70 (m, 1 H); 2.35–2.25 (m, 1 H); 2.09–2.02 (m, 1 H); 1.95–1.78 (m, 2 H); 1.48 (s, 3 H).

NOE's between the substituents of the ring confirm the stereochemistry as shown. The methine at 3.97 ppm (NC<u>H</u>CHO) is known to be S as derived from the L amino acid derivative. When the methine at 3.78 ppm (NC<u>H</u>Me) is irradiated, an enhancement is observed at the opposite methine at 3.97 ppm, thus confirming the cis relationship between the two methines. When the methine at 3.97 ppm (NC<u>H</u>CHO) is irradiated, an enhancement is observed at the aromatic protons at 7.47 and 7.21 ppm, thus confirming the stereochemistry of the phenyl as shown.

EXAMPLE 2

: 2(S)-[(3,4-dichlorophenyl)-(S)hydroxymethyl]-5 (S)-ethyl-pyrrolydine-1-carboxylic acid {4-[(2,2-dimethyl-propionylamino)-methyl]-phenyl}-amide

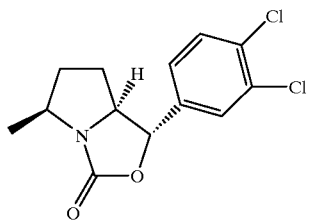

EXAMPLE 1b

1(S)-(3,4-dichloro-phenyl)-5(S)-methyl-tetrahydro-pyrrolo[1,2(S)-c]oxazol-3-one

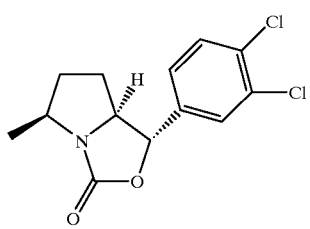

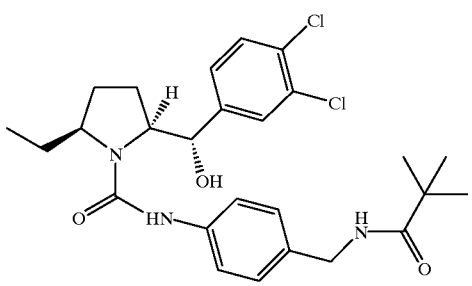

2(S)-[(3,4-dichlorophenyl)-(S)hydroxymethyl]-5(S)-ethyl-pyrrolydine-1-carboxylic acid {4-[(2,2-dimethyl-propionylamino)-methyl]-phenyl}-amide is prepared using a similar procedure as described in example 1a, starting from N-methoxylcarbonyl-5(RS)-ethyl-pyrrolydine-2(S)-carboxylic acid methyl ester which is prepared as a diastereomeric mixture at C-5, according to the procedure of Y. Kikugawa et al (*Tetrahedron Lett.* 1997, 38, 6677–6680).

MS (FAB): M+1 506.3 for $C_{26}H_{33}Cl_2N_3O_3$

EXAMPLE 3a

2(S)-[(3,4-dichlorophenyl)-(S)hydroxymethyl]-pyrrolydine-1-carboxylic acid {4-[(2,2-dimethyl-propionylamino)-methyl]-phenyl}-amide

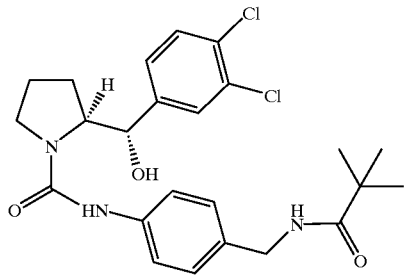

2(S)-[(3,4-dichlorophenyl)-(S)hydroxymethyl]-pyrrolydine-1-carboxylic acid {4-[(2,2-dimethyl-propionylamino)-methyl]-phenyl}-amide is prepared using a similar procedure as described in example 1a, starting from L-proline, and using the upper Rf material resulting from the ketone reduction.

MS (FAB): M+1 478 for $C_{24}H_{29}Cl_2N_3O_3$

HPLC (Zorbax SB-C18 4.6 mm×15 cm, 5% acetonitrile in water containing 0.1% phosphoric acid to 95% over 15 min at 1 ml/min) Rt 13 min

EXAMPLE 3b

2(S)-[(3,4-dichlorophenyl)-(R)hydroxymethyl]-pyrrolydine-1-carboxylic acid {4-[(2,2-dimethyl-propionylamino)-methyl]-phenyl}-amide

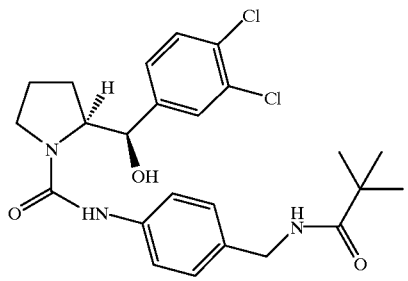

2(S)-[(3,4-dichlorophenyl)-(R)hydroxymethyl]-pyrrolydine-1-carboxylic acid {4-[(2,2-dimethyl-propionylamino)-methyl]-phenyl}-amide is prepared using a similar procedure as described in example 1a, starting from L-proline, and using the lower Rf material resulting from the ketone reduction.

MS (FAB): M+1 478 for $C_{24}H_{29}Cl_2N_3O_3$

HPLC (Zorbax SB-C18 4.6 mm×15 cm, 5% acetonitrile in water containing 0.1% phosphoric acid to 95% over 15 min at 1 ml/min) Rt=12.7 min

EXAMPLE 3c

2(R)-[(3,4-dichlorophenyl)-(S)hydroxymethyl]-pyrrolydine-1-carboxylic acid {4-[(2,2-dimethyl-propionylamino)-methyl]-phenyl}-amide

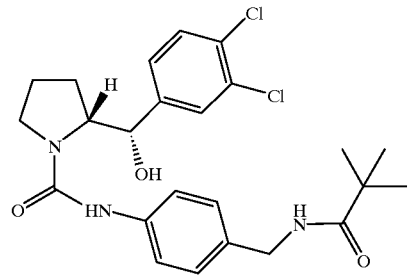

2(R)-[(3,4-dichlorophenyl)-(S)hydroxymethyl]-pyrrolydine-1-carboxylic acid {4-[(2,2-dimethyl-propionylamino)-methyl]-phenyl}-amide is prepared using a similar procedure as described in example 1a, starting from D-proline, and using the lower Rf material resulting from the ketone reduction.

MS (FAB): M+1 478 for $C_{24}H_{29}Cl_2N_3O_3$

HPLC (Zorbax SB-$C_{18\ 4.6}$ mm×15 cm, 5% acetonitrile in water containing 0.1% phosphoric acid to 95% over 15 min at 1 ml/min) Rt=13 min

EXAMPLE 3d

2(R)-[(34-dichlorophenyl)-(R)hydroxymethyl]-pyrrolydine-1-carboxylic acid {4-[(2,2-dimethyl-propionylamino)-methyl]-phenyl}-amide

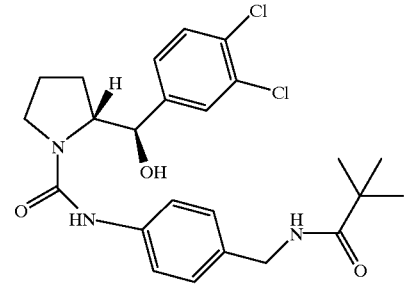

2(R)-[(3,4-dichlorophenyl)-(R)hydroxymethyl]-pyrrolydine-1-carboxylic acid {4-[(2,2-dimethyl-propionylamino)-methyl]-phenyl}-amide is prepared using a similar procedure as described in example 1a, starting from D-proline, and using the upper Rf material resulting from the ketone reduction.

MS (FAB): M+1 478 for $C_{24}H_{29}Cl_2N_3O_3$

HPLC (Zorbax SB-C18 4.6 mm×15 cm, 5% acetonitrile in water containing 0.1% phosphoric acid to 95% over 15 min at 1 ml/min) Rt=12.7 min

EXAMPLE 4a

2(S)-[(3,4-dichlorophenyl-(S)hydroxymethyl] piperidine-1-carboxylic acid {4-[(2,2-dimethyl-propionylamino)-methyl]-phenyl}-amide

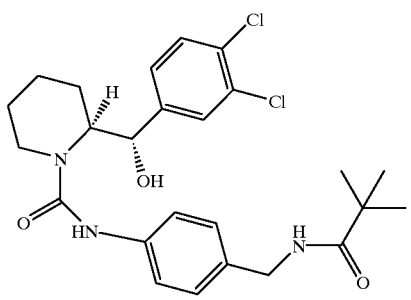

2(S)-[(3,4-dichlorophenyl)-(S)hydroxymethyl]-piperidine-1-carboxylic acid {4-[(2,2-dimethyl-propionylamino)-methyl]-phenyl}-amide is prepared using a similar procedure as described in example 1a, starting from L-pipecolic acid.

CHN calc. for $C_{25}H_{31}Cl_2N_3O_3$ and 0.3 mol hexane, 0.15 mol water: C 61.78, H 6.87, N 8.07; found: C61.79, H 6.92, N 8.11.

HPLC (Zorbax SB-C18 4.6 mm×15 cm, 5% acetonitrile in water containing 0.1% phosphoric acid to 95% over 15 min at 1 ml/min) Rt=11.3 min

EXAMPLE 4b

2(S)-[(3,4-dichlorophenyl]-(R)hydroxymethyl9-piperidine-1-carboxylic acid {4-[(2,2-dimethyl-propionylamino)-methyl]-phenyl}-amide

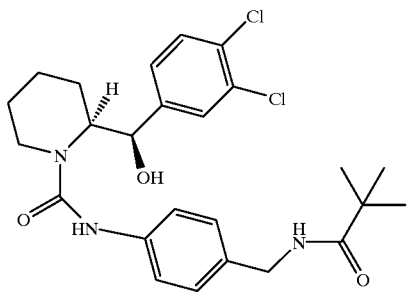

2(S)-[(3,4-dichlorophenyl)-(R)hydroxymethyl]-piperidine-1-carboxylic acid {4-[(2,2-dimethyl-propionylamino)-methyl]-phenyl}-amide is prepared using a similar procedure as described in example 1a, starting from L-pipecolic acid.

MS (FAB): M+1 492.2 for $C_{25}H_{31}Cl_2N_3O_3$

HPLC (Zorbax SB-C18 4.6 mm×15 cm, 5% acetonitrile in water containing 0.1% phosphoric acid to 95% over 15 min at 1 ml/min) Rt=11.4 min

EXAMPLE 5

4(R)-[(3,4-dichlorophenyl)-(S)hydroxymethyl]-thiazolidine-3-carboxylic acid {4-[(2,2-dimethyl-propionylamino)-methyl]-phenyl}-amide

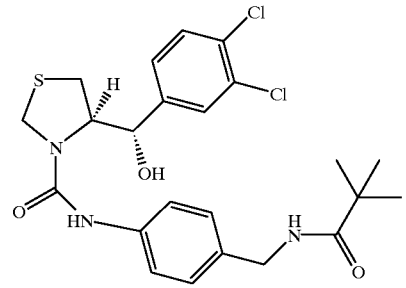

4(R)-[(3,4-dichlorophenyl)-(S)hydroxymethyl]-thiazolidine-3-carboxylic acid {4-[(2,2-dimethyl-propionylamino)-methyl]-phenyl}-amide is prepared using a similar procedure as described in example 1a, starting from L-thioproline.

MS (FAB): M+1 496.1 for $C_{23}H_{27}Cl_2N_3O_3S$

EXAMPLE 6

4(R)-[(3,4-dichlorophenyl)-(S)hydroxymethyl]-1-oxo-thiazolidine-3-carboxylic acid {4-[(2,2-dimethyl-propionylamino)-methyl]-phenyl}-amide

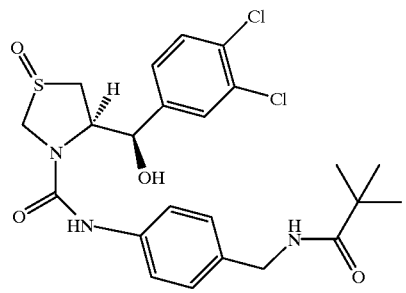

To a solution of 4(R)-[(3,4-dichlorophenyl)-(S) hydroxymethyl]-thiazolidine-3-carboxylic acid {4-[(2,2-dimethyl-propionylamino)-methyl]-phenyl}-amide (11 mg, 0.022 mmol) in MeOH (2 ml) is added sodium periodate (4.9 mg, 0.023 mmol) in water (0.5 ml). The reaction mixture is stirred at 25° C. for 18 hrs. More aqueous sodium periodate is added by portions until almost complete conversion of the starting material. The reaction mixture is filtered on cellite and concentrated in vacuo. The residue is taken into methylene chloride, washed with water and brine, concentrated and purified by preparative reverse phase HPLC and flash chromatography (silica gel, 2% to 5% MeOH/NH3 in methylene chloride) sequentially to give the following two products isomeric at the sulfoxide center:

4(R)-[(3,4-dichlorophenyl)-(S)hydroxymethyl]-1-oxo-thiazolidine-3-carboxylic acid {4-[(2,2-dimethyl-propionylamino)-methyl]-phenyl}-amide isomer A (2.5 mg):

MS (FAB): M+1 512 for C23H27Cl2N3O4S

HPLC (Zorbax SB-C18 4.6 mm×15 cm, 5% acetonitrile in water containing 0.1% phosphoric acid to 95% over 15 min at 1 ml/min) Rt=9.9 min 4(R)-[(3,4-dichlorophenyl)-(S)hydroxymethyl]-1-oxo-thiazolidine-3-carboxylic acid {4-[(2,2-dimethyl-propionylamino)-methyl]-phenyl}-amide isomer B (1.4 mg):

MS (FAB): M+1 512 for $C_{23}H_{27}Cl_2N_3O_4S$

HPLC (Zorbax SB-C18 4.6 mm×15 cm, 5% acetonitrile in water containing 0.1% phosphoric acid to 95% over 15 min at 1 ml/min) Rt=10.7 min

EXAMPLE 7

2(S)-[(3,4-dichlorophenyl)-(S)hydroxymethyl]-4(R)-hydroxy-pyrrolydine-1-carboxylic acid {4-[(2,2-dimethyl-propionylamino)-methyl]-phenyl}-amide

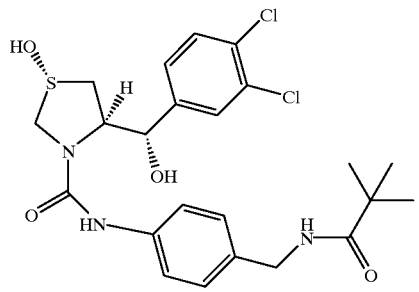

2(S)-[(3,4-dichlorophenyl)-(S)hydroxymethyl]-4(R)-hydroxy-pyrrolydine-1-carboxylic acid {4-[(2,2-dimethyl-propionylamino)-methyl]-phenyl}-amide is prepared using a similar procedure as described in example 1a, starting from trans-4-hydroxy-L-proline.

MS (FAB): M+1 494.2 for $C_{24}H_{29}Cl_2N_3O_4$

EXAMPLE 8

2(S)-[(3,4-dichlorophenyl)-(S)hydroxymethyl]-4(R)-methoxy-pyrrolydine-1-carboxylic acid {4-[(2,2-dimethyl-propionylamino)-methyl]-phenyl}-amide

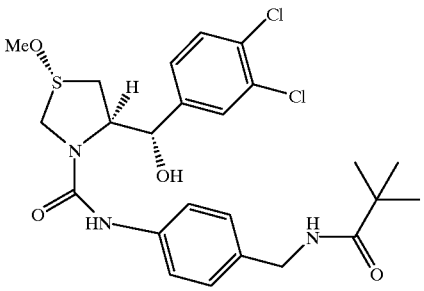

2(S)-[(3,4-dichlorophenyl)-(S)hydroxymethyl]-4(R)-methoxy-pyrrolydine-1-carboxylic acid {4-[(2,2-dimethyl-propionylamino)-methyl]-phenyl}-amide is prepared using a similar procedure as described in example 1a, starting from trans-4-methoxy-L-proline, which is obtained via methylation of trans-4-hydroxy-L-proline using methyl iodide and silver oxide in acetone.

MS (FAB): M+1 508.1 for $C_{25}H_{31}Cl_2N_3O_4$

EXAMPLE 9

3-(3,4-dichlorophenyl)-3-hydroxy piperidine-1-carboxylic acid {4-[(2,2-dimethyl-propionylamino)-methyl]-phenyl}-amide

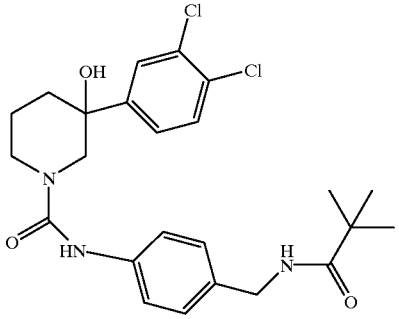

To a solution of 3-hydroxypiperidine hydrochloride (827 mg, 6 mmol) in dioxane (12 ml) and water (6 ml) cooled to 0° C. is added 1 N NaOH (12 ml, 12 mmol) and dit-butyl carbonate (827 mg, 6 mmol) in dioxane (35 ml) and the reaction mixture is stirred at 25° C. for 1 hr. The reaction mixture is diluted with ethyl acetate, washed with aqueous sodium bicarbonate, 1 N $KHSO_4$, water and brine, dried over sodium sulfate and concentrated in vacuo. The crude product is purified by flash chromatography (silica gel, 50% ethyl acetate in hexane) to give N-t-butoxycarbonyl-3-hydroxypiperidine (1.07 g).

To a solution of give N-t-butoxycarbonyl-3-hydroxypiperidine (1.07 g, 5.23 mmol) in 1:1 dimethyl sulfoxide:water (50 ml) is added triethyl amine (3.7 ml) and sulfur trioxide pyridine complex (4.24 g, 26.6 mmol). The reaction mixture is stirred at 25° C. for 3 hrs. The reaction mixture is diluted with ethyl acetate, washed with 1 N $KHSO_4$, water and brine, dried over sodium sulfate and concentrated in vacuo. The crude product is purified by flash chromatography (silica gel, 50% ethyl acetate in hexane) to give N-t-butoxycarbonyl-3-ketopiperidine (598 mg).

$^1$H NMR (CDCl$_3$, 300 MHz): δ3.95 (s, 2 H); 3.55 (t, 2 H); 2.42 (t, 2 H); 2.00–1.85 (m, 2 H); 1.40 (s, 9 H).

To a solution of 3,5-dichloro iodobenzene (1.8 g, 6.6 mmol) in diethyl ether (20 ml) cooled to −78° C. is added n-BuLi (2.8 ml of a 2.5 M solution in hexane, 6.8 mmol). The reaction mixture is stirred at −78° C. for 10 min, allowed to warm to 25° C. and added in three portions to a solution of N-t-butoxycarbonyl-3-ketopiperidine (598 mg, 3.01 mmol) in diethyl ether (10 ml) cooled to 0° C. The reaction mixture is stirred at 25° C. for 30 min. The reaction mixture is diluted with ethyl acetate, washed with 1 N $KHSO_4$, water and brine, dried over sodium sulfate and concentrated in vacuo. The crude product is purified by flash chromatography (silica gel, 30% to 50% ethyl acetate in hexane) to give N-t-butoxycarbonyl-3-(3,4-dichlorophenyl)-3-hydroxy piperidine (150 mg).

Through a solution of N-t-butoxycarbonyl-3-(3,4-dichlorophenyl)-3-hydroxy piperidine (150 mg, 0.44 mmol) in ethyl acetate (5 ml) cooled to 0° C. is bubbled HCl (g) for 5 min. The reaction mixture is stirred at 25° C. until reaction completion. The reaction mixture is concentrated in vacuo and flushed with ethyl acetate/concentrated 3 times to provide 3-(3,4-dichlorophenyl)-3-hydroxy piperidine hydrochloride which is converted without further purification to 3-(3,4-dichlorophenyl)-3-hydroxy piperidine-1-carboxylic acid {4-[(2,2-dimethyl-propionylamino)-methyl]-phenyl}-amide using N-(4-isocyanato-benzyl)-2,2-dimethyl-propionamide as described in example 1a.

MS (FAB): M+1 478.1 for $C_{24}H_{29}Cl_2N_3O_3$

Therapeutic Treatment

Compounds of the invention may be administered to patients where inhibition of human or mammalian platelet aggregation or adhesion is desired.

Compounds of the invention are useful in inhibiting platelet aggregation and thus, they may find utility in surgery on peripheral arteries (arterial grafts, carotid endaterectomy) and in cardiovascular surgery where manipulation of arteries and organs, and/or the interation of platelets with artificial surfaces, leads to platelet aggregation and consumption. The aggregated platelets may form thrombi and thromboemboli. Compounds of the invention may be administered to these surgical patients to prevent the formation of thrombi and thromboemboli.

EXAMPLE 10

Tablet Preparation

Tablets containing 25.0, 50.0, and 100.0 mg., respectively, of the active drug 2(S)-[(3,4-dichlorophenyl)-(S)hydroxymethyl]-5(S)-methyl-pyrrolydine-1-carboxylic acid {4-[(2,2-dimethyl-propionylamino)-methyl]-phenyl}-amide are prepared as illustrated below:

| TABLE FOR DOSES CONTAINING FROM 25–100 MG OF THE ACTIVE COMPOUND | | | |
|---|---|---|---|
| | Amount-mg | | |
| Active Drug | 25.0 | 50.0 | 100.0 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active drug, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 11

Intravenous Formulations

An intravenous dosage form of active drug 2(S)-[(3,4-dichlorophenyl)-(S)hydroxymethyl]-5(S)-methyl-pyrrolydine-1-carboxylic acid {4-[(2,2-dimethyl-propionylamino)-methyl]-phenyl}-amide is prepared as follows:

| Ingredient | Amount |
|---|---|
| Active Drug | 0.5–10.0 mg |
| Sodium Citrate | 5–50 mg |
| Citric Acid | 1–15 mg |
| Sodium Chloride | 1–8 mg |
| Water for Injection (USP) | q.s. to 1 L |

Utilizing the above quantities, the active drug is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md., copyright 1994.

EXAMPLE 12

Intravenous Formulation

A pharmaceutical composition was prepared at room temperature using, a citrate buffer, and sodium chloride, to obtain a concentration of of 0.25 mg/ml.

800 grams of water was introduced into a standard pharmaceutical mixing vessel. 0.25 grams of active drug 2(S)-[(3,4-dichlorophenyl)-(S)hydroxymethyl]-5(S)-methyl-pyrrolydine-1-carboxylic acid {4-[(2,2-dimethyl-propionylamino)-methyl]-phenyl}-amide was dissolved in the water. 2.7 grams sodium citrate and 0.16 grams citric acid were added to obtain a finished citrate concentration of 10 mM. 8 grams of sodium chloride was added. 200 grams of water was then added to achieve the desired final concentrations of ingredients. The resulting aqueous formulation had the following concentrations:

| Ingredient | Amount |
|---|---|
| Active drug | 0.25 mg/ml |
| citrate buffer | 10 mM |
| sodium chloride | 8 mg/ml |

The finished concentrated formulation is stored in a standard USP Type I borosilicate glass container at 30–40 degrees C. Prior to compound administration, the concentrated formulation is diluted in a 4:1 ratio resulting in a finished concentration of 0.05 mg/ml and transferred to an infusion bag.

What is claimed is:

1. A compound having the formula

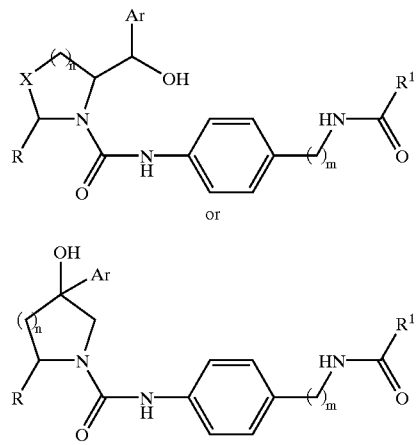

or a pharmaceutically acceptable salt thereof, wherein m is 1;

n is 1 or 2;

R is hydrogen, or $C_{1-10}$ alkyl;

$R^1$ is $C(CH_3)_3$;

X is
CH₂,
S,
SO,
CHOH,
CHOCH₃; and
Ar is
aryl, unsubstituted, monosubstituted with halogen, or disubstituted same or different, with halogen.
2. A compound of claim 1, or a pharmaceutically acceptable salt thereof, wherein.
R is
hydrogen,
CH₃, or
CH₂CH₃; and
Ar is
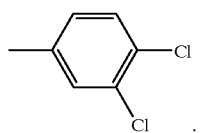
3. A compound of claim 2, or a pharmaceutically acceptable salt thereof, selected from the group consisting of
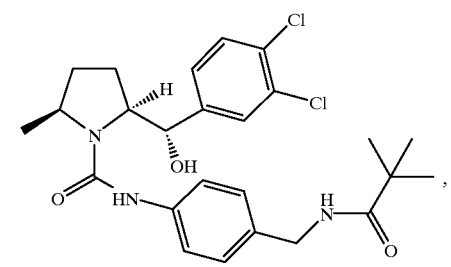
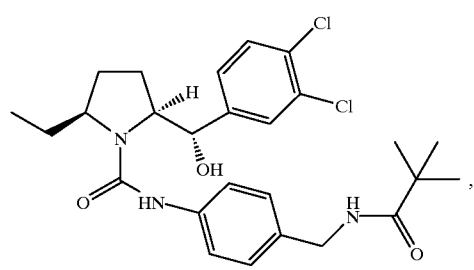
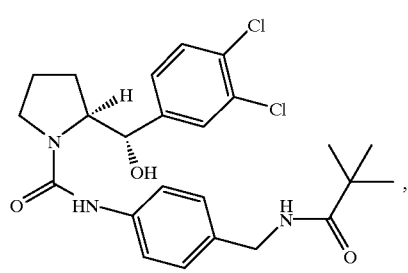
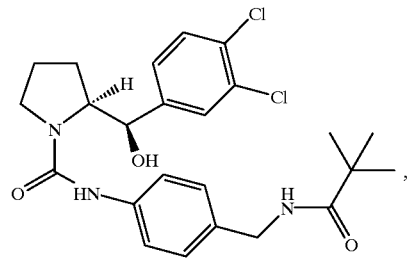
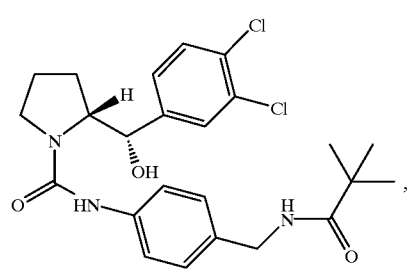
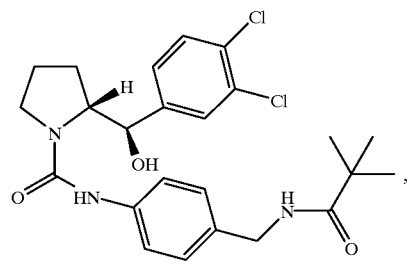
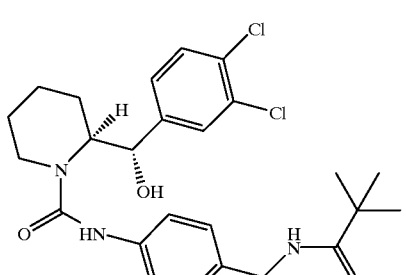
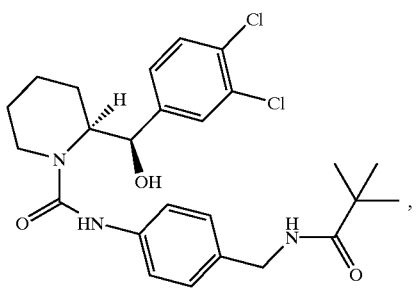

25
-continued
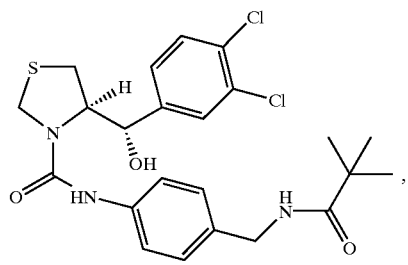
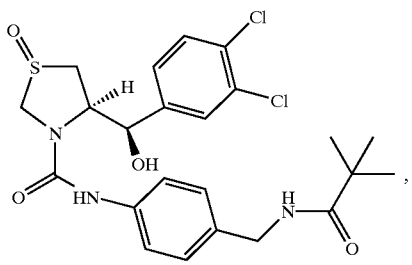
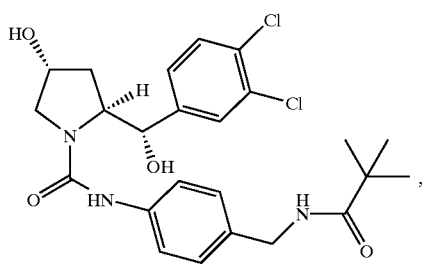
26
-continued
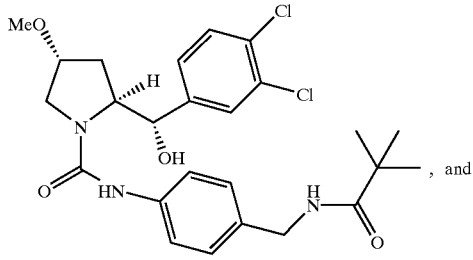, and
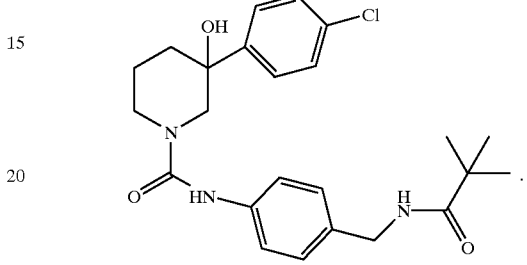.
4. A pharmaceutical composition comprising a therapeutically effective amount of a compound of claim 1 and a pharmaceutically acceptable carrier.
5. A method for inhibiting the aggregation of blood platelets in a mammal, by blocking thrombin from acting at its receptor site, comprising treating the mammal with a composition of claim 4.
* * * * *